(12) United States Patent
Plochocka

(10) Patent No.: US 6,464,961 B2
(45) Date of Patent: Oct. 15, 2002

(54) POLYMERIC DELIVERY AND RELEASE SYSTEMS FOR ORAL CARE ACTIVES

(75) Inventor: Krystyna Plochocka, Scotch Plains, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/921,186

(22) Filed: Aug. 2, 2001

(65) Prior Publication Data

US 2001/0046476 A1 Nov. 29, 2001

Related U.S. Application Data

(63) Continuation of application No. 09/568,259, filed on May 10, 2000, now Pat. No. 6,315,987.

(51) Int. Cl.[7] .............................. A61K 9/68; A61K 7/16; C08F 222/04; C09K 3/00
(52) U.S. Cl. ........................... 424/48; 424/49; 424/440; 424/486; 426/3
(58) Field of Search .............................. 424/48–58, 440, 424/486

(56) References Cited

U.S. PATENT DOCUMENTS

| | | | | | |
|---|---|---|---|---|---|
| 4,668,506 A | * | 5/1987 | Bawa | ........................ | 424/429 |
| 4,713,244 A | * | 12/1987 | Bawa | ........................ | 424/429 |
| 4,931,279 A | * | 6/1990 | Bawa | ........................ | 424/427 |
| 5,451,401 A | * | 9/1995 | Zorby et al. | ................... | 424/49 |
| 5,628,986 A | * | 5/1997 | Sanker et al. | ................. | 424/49 |
| 5,968,207 A | * | 10/1999 | Li | ................. | 8/490 |
| 6,315,987 B1 | * | 11/2001 | Plochocka | ................... | 424/49 |

OTHER PUBLICATIONS

Abstract of Chitanu Et Al 65(1): 75–85 Maleic Copolymers with Pendent Thymol, etc. 1999.*
Asakura Et Al J. Macromol. Sci. Chem A18(2): 285–297, 1982*
Yoshihara Et Al J. Polym. Sci. Polym. Chem. Ed 19(5): 1269–1272, 1981*
Fujihara Et Al. J. Polym. Sci. Polym. Lett. Ed. 17(8): 507–509, 1979.*
Kurokawa Et Al J. Polym. Sci. Polym. Ed. 17(2): 473–484, 1979.*
Matsuzaki Et Al Makromol. Chem. 164: 127–134, 1973.*
Angiolini Et Al J. Polym. Sci. Part A 32(15): 2849–2857, 1994.*

* cited by examiner

Primary Examiner—Shep K. Rose
(74) Attorney, Agent, or Firm—Walter Katz; William J. Davis; Marilyn J. Maue

(57) ABSTRACT

A polymer useful in oral care compositions which has a reactive group covalently bonded to a bactericide, flavorant and/or essential oil compound, said bond being hydrolyzable in aqueous solution to slowly release said compound into said composition.

3 Claims, No Drawings

POLYMERIC DELIVERY AND RELEASE SYSTEMS FOR ORAL CARE ACTIVES

This is a continuation, of application Ser. No. 09/568,259, filed on May 10, 2000, now U.S. Pat. No. 631,598,701.

BACKGROUND OF THE INVENTION

1. Field of the Invention

This invention relates to oral care compositions, and, more particularly, to a polymer for use in such compositions which has a reactive group therein covalently bonded to a bactericide, flavorant and/or essential oil compound, which bond is hydrolyzable in aqueous solution to slowly release the compound into the composition.

2. Description of the Prior Art

Oral care compositions such as dentifrices, denture adhesives, buccal tapes and chewing gums usually contain one or more active compounds including bacteriocidal compounds, e.g. triclosan or thymol; flavorants, e.g. menthol, thymol and essential oils. However, these active components are released immediately into the mouth, and, accordingly, are not available in the composition after use.

Accordingly, it is an object of this invention to provide an oral care composition which includes a polymer which can be used as a delivery system to slowly release an active compound over a prolonged period of time, thus extending the usefulness of such active material in such compositions.

These and other objects and features of the invention will be made apparent from the following description of the invention.

SUMMARY OF THE INVENTION

What is described herein is an oral care composition which includes a polymer having a reactive group covalently bonded to a bactericide, flavorant and/or essential oil compound, which bond is hydrolyzable in aqueous solution to slowly release said compound in said composition.

Suitable reactive groups include an acid, carboxylate, amide or ester. Suitable polymers which include said reactive group include acrylate, maleate, fumarate, vinyl pyrrolidone, vinyl caprolactam, methacrylic acid, vinyl acetate, vinyl amide, alkyl vinyl ether, maleic anhydride, dimethylaminopropyl methacrylic acid, dimethylaminopropyl methacrylamide, and alkylene polymers, and copolymers and terpolymers thereof.

Typical oral care compositions are buccal tape, denture adhesive, dentifrice, anti-plaque, mouthwash and chewing gum compositions.

DETAILED DESCRIPTION OF THE INVENTION

In accordance with the invention, there is provided herein polymers containing covalently-bound active components which can be used as delivery and release systems in oral care. Active components, such as bacteriocidal compounds (e.g. triclosan, thymol) or flavorants (e.g. menthol, thymol), or essential oils can be bound to such polymers by acid, carboxylate, ester or amide groups that can undergo aqueous hydrolysis in the mouth. Such polymers can be made by (co)polymerization of monomers containing the active compounds (e.g. acrylate, maleate, fumarate) with other monomers such as vinylpyrrolidone, (meth)acrylic acid, vinyl acetate, and the like; by esterification of carboxylic or anhydride side groups; or by transesterification of ester groups in a polymer (e.g. Gantrez® AN—maleic-anhydride-methyl vinyl ether, and Gantrez® ES (the half-ester of maleic-anhydride-methyl vinyl ether), vinylpyrrolidone-maleic anhydride copolymer, acrylic acid-maleic anhydride copolymer etc.) Polymeric products of such polymers and triclosan, menthol and thymol are preferred embodiments of the invention, which provide delivery systems in oral care compositions such as buccal tapes, denture adhesives, chewing gum and dentifrices.

The invention will be described hereinafter with reference to the following examples.

EXAMPLE 1

Preparation of the Menthyl Ester of Maleic Anhydride-Methyl Vinyl Ether Copolymer (Gantrez® AN) by Bulk Esterification Menthol crystals, 7.8 g (0.05 mol) (Hagelin) and 15.6 g (0.1 equivalent of anhydride monomer unit) of Gantrez® AN 903 BF (ISP) were placed in a capped and sealed 50 ml glass tube and heated at 140° C. for 24 hours. The reaction product changed from a powder to a partly-yellowish glass. After cooling to room temperature, the product was analyzed by $^{13}$CNMR. The presence of the mono-menthyl ester of Gantrez AN was identified in the product, and some unreacted menthol.

EXAMPLE 2

Preparation of the Menthyl Ester of Crosslinked Maleic Anhydride-Methyl Vinyl Ether Copolymer by Bulk Esterification Crosslinked maleic anhydride methyl vinyl ether, Stabileze® 06 (ISP), 15.6 g (0.1 equiv. of anhydride monomer unit) powder and 7.8 g (0.05 mol) of menthol crystals were blended in a 100 ml flask and sealed. The flask was then heated to 120° C. for 5 hours, and at 140° C. for 20 hours. The reaction product changed from a white-powder to a glassy-yellowish. FTIR spectrum analysis (solid KBr tablet) of the reaction product showed the presence of menthyl half-ester of the monomer anhydride unit, a decrease in absorbance at 1858, 1780 and 1730 cm$^{-1}$, indicating a decrease in the concentration of its anhydride unit, and the appearance of a band at 1724 cm$^{-1}$ characteristic of an ester of a secondary alcohol.

EXAMPLE 3

Hydrolysis of Products of Examples 1 and 2

The product of Example 1(2 g of finely ground powder) was slurried with Dl water (18 g) in a sealed jar. The slurry had a very faint menthol odor. It was agitated with a magnetic stirrer with gentle heat (36 to 37° C.) for 4 hours. The freeze-dried sample was evaluated by FTIR (as a KBR pellet). The results showed that the anhydride absorbance had disappeared and the ester band at 1736 cm$^{-1}$ had persisted. When kept overnight under the same conditions the ester band was significantly reduced and the slurry had a strong menthol odor.

Similar results were obtained when the product of Example 2 was used.

EXAMPLE 4

Triclosan Acrylate

Irgasan® DP300 5-chloro-2-(2,4-dichlorophenol) (triclosan), 23.5 g (0.081 mol) was dissolved in 300 ml of dry tetrahydrofuran in a 1-l jacketed kettle with agitator, addition funnel and reflux condenser. Then 10.6 ml of triethylamine was added to the solution with agitation. To the resulting solution was added dropwise 6.68 (0.0738 mol) g of acryloyl chloride. The reaction temperature was maintained at 20° C. with a circulating cooling bath. After the addition of acryloyl chloride was completed, the agitation and temperature conditions were maintained for 5 hours. Then the reaction product was kept overnight at room temperature, filtered to remove solid triethylamine hydrochloride and the filtrate rotovapped at room temperature under 100–110 mm Hg to concentrate the product. The remaining solution was dissolved in 100 ml heptane and washed with 5% $Na_2CO_3$ solution in Dl water until basic; then with Dl water until neutral. The heptane solution of the product was dried with $MgSO_4$ in a refrigerator overnight, and filtered. The filtrate contained 25.3% triclosan acrylate as determined by bromination. FTIR spectrum confirmed the presence of the unsaturated ester of a phenol (1753 $cm^{-1}$).

EXAMPLE 5

Polymerization of Triclosan Acrylate 10 ml of a heptane solution of triclosan acrylate of Example 4 was placed in a reaction tube and sparged with nitrogen. Then lauroyl peroxide (0.2 g) was added and the tube was sealed, and placed in a 65° C. bath for 8 hours. The solution then turned yellowish and slightly viscous. FTIR spectrum confirmed the polymerization of the double bond.

EXAMPLE 6

Copolymerization of Triclosan Acrylate with N-Vinylpyrrolidone 200 ml of heptane was charged into an 1-l jacketed kettle with agitator, nitrogen inlet and two addition funnels. The solvent was sparged with nitrogen for 30 minutes and heated to 65° C. then 0.2 ml of Lupersol® 11 initiator was added. Thereafter N-vinylpyrrolidone (29.97 g, 0.27 mol) and triclosan acrylate (Ex. 4) (60 g, 0.03 mol) was added dropwise over 4 hours. At the end of the monomer addition, a 0.1 ml Lupersol® 11 booster was added and the reaction was kept at 65° C. for 3 hours. The thus-precipitated polymer was filtered, washed with heptane and dried in a vacuum oven at 40° C. for 4 hours. Yield: 37.8 g of a white powder. FTIR spectrum confirmed the desired polymerization.

EXAMPLE 7

Thymyl Acrylate

Thymyl acrylate was made by reaction of 15.0 g (0.10 mol) of thymol, 9.96 g (0.11 mol) of acryloyl chloride and 12.0 g (9.118 mol) of triethylamine in 300 ml dried THF, according to Example 4. The product was a 15% solution of thymyl acrylate in heptane, with a strong FTIR absorption at 1742 $cm^{-1}$, confirming the presence of the unsaturated ester of phenol.

EXAMPLE 8

Copolymerization of Thymyl Acrylate 20 g (0.18 mol) of vinylpyrrolidone and 39.7 g (0.02 mol) of thymyl acrylate (Ex. 7) were copolymerized in hexane, using the procedure of Ex. 6. Yield: 15 g of a powdery, slightly glassy product. FTIR confirmed the disappearance of monomer double bonds.

EXAMPLE 9

Menthyl Acrylate

Menthyl acrylate was prepared by a procedure similar to Example 7. A heptane solution containing 8.9% menthyl acrylate was obtained.

EXAMPLE 10

Copolymerization of Menthyl Acrylate, N-Vinylpyrrolidone and Acrylic Acid

Hexane (300 g) in a 1-l Buchi pressure reactor was sparged with nitrogen (30 min). The reactor was heated to 65° C. and 0.25 ml of Lupersol® 11 initiator was added. While maintaining the same temperature, a blend of N-vinylpyrrolidone (75 g, 0.675 mol) with 56 g (0.024 mol) of menthyl acrylate solution (Ex. 9) and a solution of 5 g (0.07 mol) of acrylic acid in 50 g hexane was added over 3 hours using two separate syringe pumps. The temperature was held for 3 hours. After 24 hours, 1 g of Lupersol® 101 initiator was added and the reaction was held at 120° C. for 7 hours. Then the reactor was cooled, the solid polymer filtered and washed with hexane, and then dried under vacuum at 65° C. for 4 hours. Yield 66.0 g of the desired white powder product.

While the invention has been described with particular reference to certain embodiments thereof, it will be understood that changes and modifications may be made which are within the skill of the art. Accordingly, it is intended to be bound only by the following claims, in which.

What is claimed is:

1. A thymol or triclosan ester of a copolymer of maleic anhydride and methyl vinyl ether in which the thymol or triclosan is covalently bonded by esterification or transesterification to the reactive anhydride and carboxylic acid groups of the copolymer, said bond being hydrolyzable in aqueous solution to slowly release said compound in said composition.

2. A slow release, oral care composition including the polymer of claim 1.

3. An oral care composition including the polymer of claim 1 which is a buccal tape, denture adhesive, dentifrice, anti-plaque, mouthwash or chewing gum composition.

* * * * *